United States Patent

Craig et al.

[11] Patent Number: 6,015,480
[45] Date of Patent: Jan. 18, 2000

[54] CHLORIDE ION SELECTIVE MEMBRANE ELECTRODE HAVING IMPROVED STABILITY AND SELECTIVITY

[75] Inventors: Alan Robert Craig, Wilmington, Del.; Michael Patrick Reidy, Foster City, Calif.; Chengrong Wang, Hockessin, Del.

[73] Assignee: Dade Behring Inc., Deerfield, Ill.

[21] Appl. No.: 08/923,182

[22] Filed: Sep. 4, 1997

Related U.S. Application Data

[63] Continuation-in-part of application No. 08/784,880, Jan. 16, 1997, abandoned.

[51] Int. Cl.[7] .................................................. G01N 27/26
[52] U.S. Cl. ........................................ 204/418; 73/863.23
[58] Field of Search .................................. 204/415, 418; 7/416, 779; 205/778.5, 792; 435/817, 287.9; 73/863.23

[56] References Cited

U.S. PATENT DOCUMENTS

| | | | |
|---|---|---|---|
| 3,948,745 | 4/1976 | Guilbault et al. | 204/403 |
| 4,207,398 | 6/1980 | Riener | 521/31 |
| 4,287,042 | 9/1981 | Ebdon et al. | 204/418 |
| 4,361,473 | 11/1982 | Young et al. | 204/418 |
| 4,454,007 | 6/1984 | Pace | 204/1 T |
| 4,477,970 | 10/1984 | Purbrick et al. | 204/1 T |
| 4,489,612 | 12/1984 | Geist et al. | 204/416 |
| 4,597,848 | 7/1986 | Oka et al. | 204/418 |
| 4,629,744 | 12/1986 | Uematsu et al. | 521/62 |
| 4,670,127 | 6/1987 | Ritter et al. | 204/418 |
| 5,112,471 | 5/1992 | Shibata et al. | 204/418 |
| 5,116,481 | 5/1992 | Ozawa et al. | 204/290 |
| 5,401,376 | 3/1995 | Foos et al. | 204/415 |
| 5,522,978 | 6/1996 | Pace et al. | 204/418 |

FOREIGN PATENT DOCUMENTS

| | | |
|---|---|---|
| 55075643 | 6/1980 | Japan . |
| 59-182357 | 10/1984 | Japan . |
| 61-79153 | 4/1986 | Japan . |

OTHER PUBLICATIONS

English language translation of Kazuo et al. (JP 55075643), 1980.
WPIDS abstract of Kazuo et al. (JP 55075643 A), Jun. 7, 1980.
JAPIO abstract Kazuo et al. (JP 55075643 A), Jun. 7, 1980.
Egorov, et al.; *Zh. Anal. Khim.*; The Effect of Ion Association on the Selectivity of Electrodes Reversible with Respect to Organic Cations; 47–9:1685–1692; 1992 Caplus abstract, month unknown.
Yamashita, et al.; *Patent Abstracts of Japan*; Chlorine Ion Selective Electrode and Sensitive Film; 18–3:161; 1994, month unknown.

*Primary Examiner*—Robert Warden
*Assistant Examiner*—Alex Noguerola
*Attorney, Agent, or Firm*—Leland K Jordan; Lois K Ruszala

[57] ABSTRACT

A method for extending the uselife of a chloride ion selective membrane of an ISE sensor by providing a two-layer sensor structure wherein an quaternized ion-selective polymeric layer is positioned between a sample to be analyzed and a conventional polymeric ISE membrane containing an ion-exchange agent. Also provided are polymer compositions comprised methyl methacrylate/choloromethyl styrene copolymer and mixtures thereof that have been reacted with tertiary amines.

7 Claims, 3 Drawing Sheets

CHLORIDE ION SELECTIVE MEMBRANE ELECTRODE HAVING IMPROVED STABILITY AND SELECTIVITY

This application is a continuation-in-part of U.S. application Ser. No. 08/784,880, filed Jan. 16, 1997, now abandoned.

BACKGROUND OF THE INVENTION

1. Field of the Invention

This invention relates generally to ion sensors, and more particularly relates to chloride ion-selective-electrode sensors and for methods for production of sensors having improved selectivity and stability in repeated use.

2. Description of the Related Art

Solid state ion-selective-electrode (ISE) sensors that measure the activity or concentration of analyte ions and metabolites are useful in the analysis of biological sample fluids including blood, urine, plasma, saliva, spinal fluid, and serum. Such sensors often use a polymeric membrane incorporating an ion-selective agent or ion-sensing element with the ability to complex or otherwise attach to the desired analyte and produce an electrical response. The magnitude of the electrical response to the analyte is defined as the sensitivity. In use, sample fluids are brought into direct contact with the membrane layer requiring that the membrane's sensitivity remain constant during repeated exposure to fluids, elsewise the sensor will produce inaccurate or spurious measurements and have a limited uselife. Sensors that measure chloride ions often use tridodecylmethylammonium chloride (TDMAC) as an ionophore. Unfortunately, the fluids in contact with the sensor can extract the TDMAC out of the membrane causing the sensitivity uselife of thin ISE sensors to be limited. This is particularly problematic when heparinized plasma samples are analyzed, because the heparin has been found to adversely affect TDMAC, possibly by extraction of TDMAC or contamination of the sensor surface or other mechanisms, and has been determined to limit the sensor life to about 200 uses. Uselife is generally defined as the exposure of the sensor to fluids that is required to cause a change in the calibration slope by more than 10%. Herein, uselife is defined by the number of hours a sensor is in contact with a standard test fluid comprising a standard aqueous solution of sodium and potassium chloride and carbonate having a pH in the range about 9.0 to 9.5 and an ionic strength of approximately 150 millimolar or as the number of plasma samples required to cause this change.

Another requirement of the sensor is having a minimal response to species in samples other than the analyte of interest, a characteristic known as selectivity. Body fluids, urine and blood in particular, often contain substances such as drugs and various ionic species which can also complex or attach to the membrane and so produce a spurious electrical response. In the design of sensors that determine the chloride content in blood and urine, a particularly difficult challenge is achieving a high selectivity over ions like salicylates (in blood and urine) and/or other similar ions. and maintaining this selectivity during repeated exposure to blood and urine samples.

There is general theoretical understanding of the requirements for producing sensitivity within an ISE sensor membrane, however, theory has poor predictive value for defining the chemical structure of a membrane required to obtain good initial sensitivity and selectivity and to retain these characteristics during actual use.

It is known to improve the selectivity of an ISE sensor by employing a plasticizer having an alkyl or phenyl group to which a "functional group" bonds (U.S. Pat. No. 5,112,471). This approach uses a high dielectric constant plasticizer in order to maintain a favorable ionic dissociation.

It is also known to improve the selectivity and accuracy of anion-selective membranes by using tetra-alkyl, quaternary phosphonium salts having four relatively large alkyl radicals. Such salts have a relatively low positive charge density and greater steric hindrance, which results in weaker interactions with ions which sometimes improves selectivity for large hydrophobic ions (U.S. Pat. No. 5,116,481).

Other efforts to improve the durability of sensors used a semi-permeable membrane to protect an underlying electrolyte layer from species such as metal ions, which may prove harmful to their intended operation, while passing species such as water vapor and oxygen necessary for their operation (U.S. Pat. No. 5,401,376). Such membranes are provided with a degree of flexibility to allow the underlying electrolyte layer to swell and contract while adhering to that layer.

It is evident from the foregoing that a remaining shortcoming in chloride ISE sensors is degradation in the sensor membrane's sensitivity and selectivity as a result of repeated exposure to sample fluids containing the analyte of interest as well as substances other than the analyte of interest. In addition, extending the uselife of a chloride sensor by increasing the stability of its selectivity without adversely affecting the sensor's sensitivity is of commercial interest and also presents significant design challenges.

SUMMARY OF THE INVENTION

The present invention improves the selectivity and extends the uselife of chloride ISE sensors. In this invention, the sample to be analyzed contacts a polymeric membrane to which cationic ion-exchange sites are covalently bound. This membrane is positioned over a conventional ISE membrane containing non-covalent ion carriers to form a bi-layer membrane structure. In an exemplary embodiment of the present invention, the top layer of the bi-layer membrane incorporates an optimized concentration of covalent quaternary ammonium groups therein, to withstand repeated exposures to test fluids, thereby maintaining membrane sensitivity, especially during exposures to heparinized plasma samples. It has been unexpectedly found that the selectivity of the two-layer sensor membrane having the quaternized layer is superior to the conventional membrane without the polymeric quaternized layer. The selectivity has been determined to be dependent upon the actual number of covalently bound ion-exchange sites. In an alternate exemplary embodiment, a sensor membrane comprising only the quaternized layer has been found to have improved ionic selectivity, the quaternized layer also comprising immobilized ion-exchange site to respond to anions present in the sample, in the absence of a conventional ISE membrane containing chloride ion-exchange sites.

DETAILED DESCRIPTION OF THE INVENTION

Figure 1:
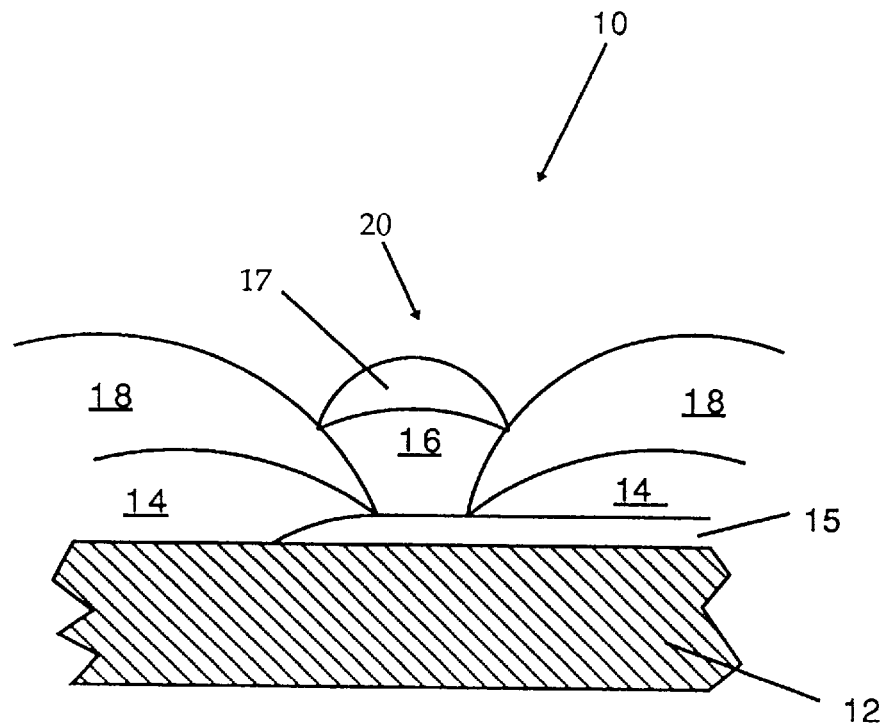
FIG. 1 is a cross sectional view of a sensor illustrating a membrane structure exemplary of the present invention.
Figure 1A:
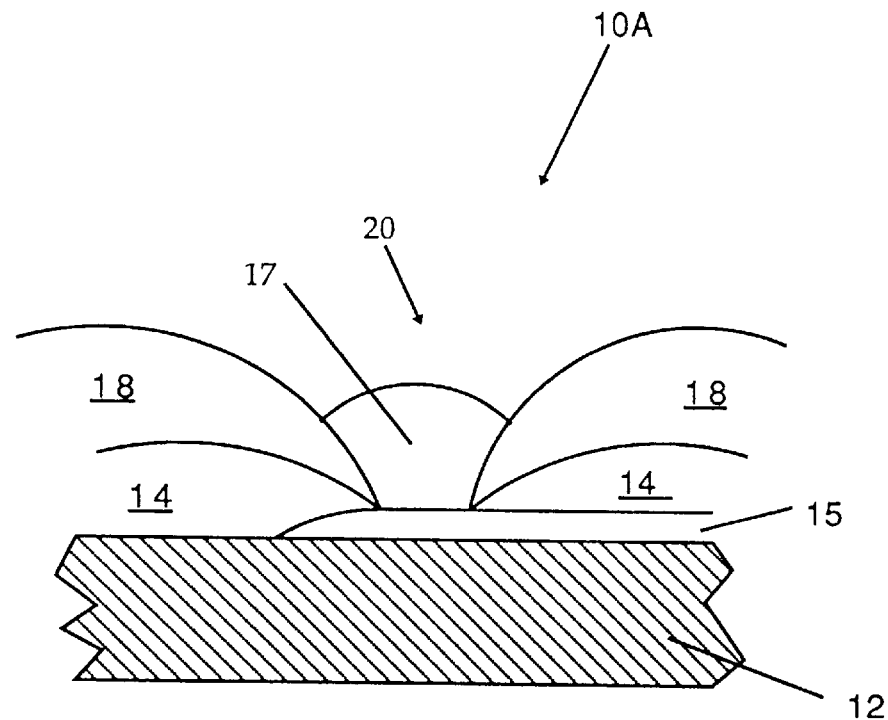
FIG. 1A is a cross sectional view of a sensor illustrating an alternate membrane structure exemplary of the present invention.

FIG. 1 shows an ISE sensor 10 comprising a first dielectric layer 14 and a second dielectric layer 18 formed on a sensor base 12 in contact with a conductive electrode 15, the layers 14 and 18 having patterns of openings, the openings aligned to form a cavity within layers 14 and 18, generally indicated by the numeral 20. A conventional sensor membrane layer 16 incorporating an effective amount of a chloride ion-sensing element is applied within the cavity 20 in contact with the conductive path 15. A polymeric sensor membrane layer 17 incorporating an effective concentration of quaternary ammonium groups as described hereinafter is coated over the conventional sensor membrane layer 16 so as to be positioned between layer 16 and the fluids to be tested. The process for making such a sensor, preferably using conventional thick film screen printing techniques and suitable drying means, is well known in the art, for example, as described in U.S. Pat. No. 4,454,007, assigned to the assignee of the present invention. The purpose of the dielectric layers 14 and 18 is to provide sufficient depth to cavity 20, generally between 20 and 40 microns, to accommodate the required thickness of sensor membrane layers 16 and 17. An interfacial layer, not shown, composed of a conductive metal and conductive metal-salt compounds may optionally be disposed between the conductor layer 15 and the sensor membrane layer 16 to stabilize that interface. FIG. 1A shows an alternate ISE sensor 10A comprising a first dielectric layer 14 and a second dielectric layer 18 formed on a sensor base 12 in contact with a conductive electrode path 15, the layers 14 and 18 having patterns of openings, the openings aligned to form a cavity, generally indicated by the numeral 20. Only polymeric sensor membrane layer 17 incorporating an effective concentration of quaternary ammonium groups as described hereinafter is applied within the cavity 20 in contact with the conductive path 15.

The sensors 10 of the present invention are useful for the potentiometric determination of chloride ions in biological test fluids including blood, urine, plasma, saliva, spinal fluid, and serum. Such fluids, particularly urine samples, often contain various substances such as drugs and drug metabolites (e.g. acetyl salicylate, and salicylate) which can interfere with the determination of the ions to be determined. In addition, many blood samples have been heparinized to prevent coagulation and this compound has been observed to prematurely shorten the membrane's uselife. As described previously, a primary requirement of the membrane layer 16 is that it have good initial selectivity and sensitivity to the analyte ion of interest, and that it retain these properties during repeated exposures to test fluids having these species.

A variety of ion selective membrane paste compositions may be used to form the conventional sensor membrane layer 16, generally comprising an ion-selective agent or ion-sensing element for a chloride ion-to provide the desired selectivity and sensitivity, a solvent capable of dissolving the ion-sensing element and a supporting matrix comprised of one or more binder materials. The binder matrix can be any material which is capable of forming a film of sufficient permeability to produce, in combination with the ion-sensing element and solvent, ion-exchange capability across the film, as well as retain membrane integrity during repeated exposures to test fluids. The solvent used can be any solvent commonly used to prepare conventional membranes. Optionally, a suitable amount of plasticizer, as well as other components, such as fumed silica and silanes may be included in the membrane. The plasticizer, if included, can be added to the polymer along with the ionophore. Useful "chloride ion-selective agents or ionophores" include any substance which provides for selective interaction with chloride. TDMAC (tridodecylmethylammonium chloride) is a particularly useful chloride ionophore. U.S. Pat. No. 5,401,376 contains information about the various chemical constituents and applicable production processes useful in production of ISE sensors having an ion-sensitive member in direct contact with an electrical conductor and is generally indicative of the state-of-the art.

A variety of paste compositions may be used for the polymeric quaternized layer 17 of the present invention, generally comprising a quaternized ammonium salt moiety linked to the backbone structure of a high molecular weight polymer such as a methyl methacrylate/choloro-methyl styrene copolymer. The process used to make the paste is a two step polymer synthesis followed by formulation with solvent. The first step of the synthesis is semi-continuous batch emulsion co-polymerization of chloro-methylstyrene with methyl methacrylate optionally using tertiary-dodecylmercaptan as a chain transfer agent to limit the molecular weight. The product of this polymerization, prepolymer, is reacted with an amine, such as tributylamine or triethylamine, to make a polymeric quaternary ammonium salt. After purification, this is dissolved in solvent at a suitable concentration to make paste. Analytical measurements can be done to determine the molecular weight of the intermediate product, as well as the degree of quaternization of the finished quaternized product, or other properties of interest, e.g., Tg. The selectivity of the finished chloride sensors 10 and 10A has been found to be satisfactory when dichloromethane is the reaction solvent, and organic solvents are used for the purification.

The volatile solvent is used to aid manufacturing of the membrane. Such a solvent lowers the viscosity of the membrane composition to facilitate application of the membrane to the sensor. The solvent is removed in the drying step described below. Useful solvents for this purpose include known solvents for the polymeric binders described above. In the case of carboxylated PVC, isophorone is a preferred solvent. Cyclohexanone, dimethylformamide, or other highly polar solvents may also be used.

The sensor design, the substrate and the polymeric paste used to prepare the undried membranes were prepared according to the process described in U.S. Pat. No. 5,522,978 assigned to the assignee of the present invention and hereby incorporated by reference. By way of example, one first deposits the conductor paths 15 on the sensor base 12, typically using a conventional silver conductor paste, for instance series QS175, available from E. I. du Pont de Nemours & Co., Wilmington, Del., then the first dielectric layer 14, typically a conventional ceramic dielectric paste, for instance series QS482, the second dielectric layer 18 also for instance series QS482, and finally the sensor membrane layer 16. Acceptable materials for the sensor bases 12 are alumina, glass, or glass-epoxy composites. A chloride-selective sensor paste may be dispensed using a syringe onto the electrical conductor 15 at the chloride-selective ISE sensor location 10-Cl to form the ion-selective membrane of the chloride ISE sensor as also depicted in FIGS. 1 and 1A.

Figure 3:
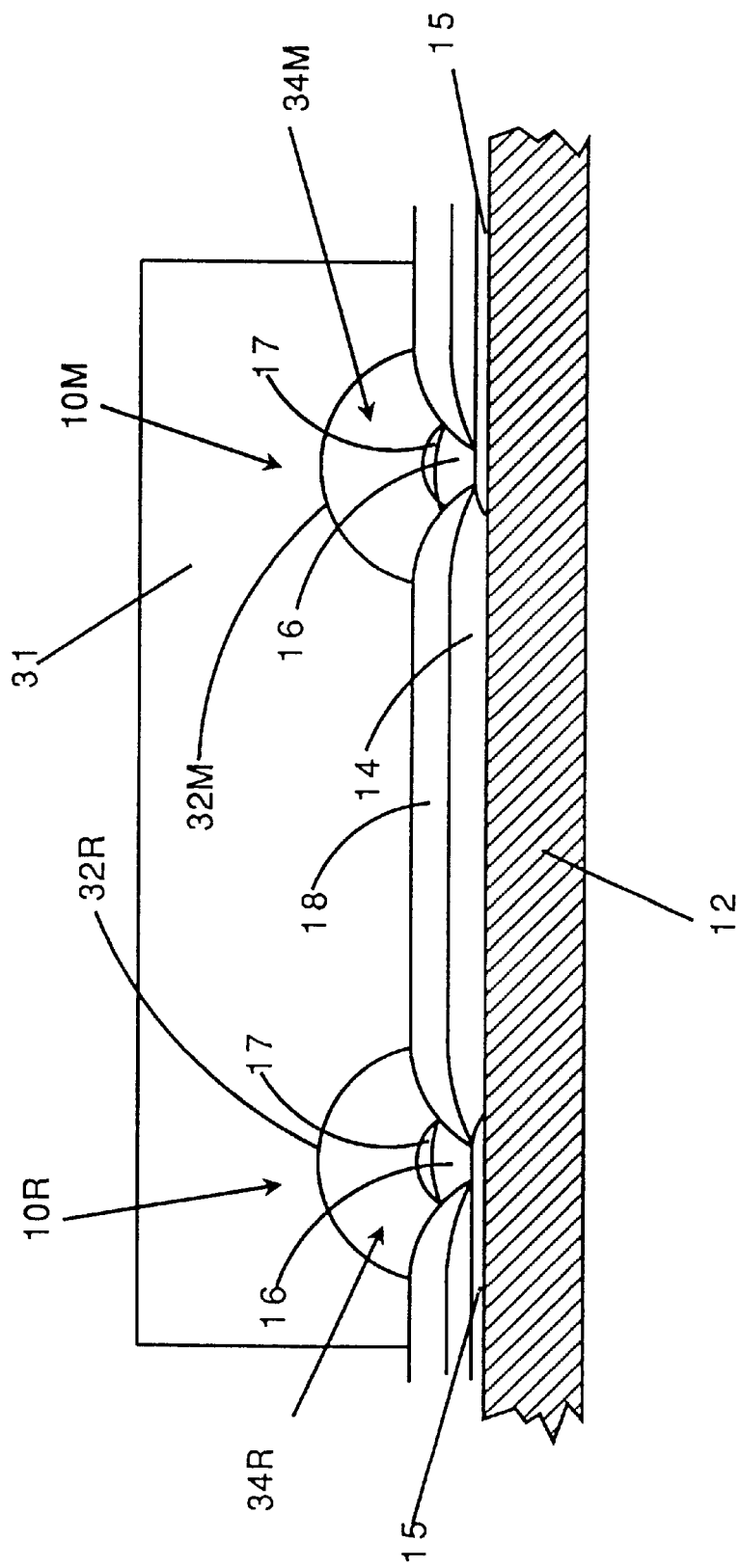

The membrane paste compositions are typically dried by heating at a temperature in the range 80° to 110° C. for between 10 and 90 minutes to form ion-selective membrane layer 16 and quaternized layer 17. The resulting sensors 10 are then positioned against a flow channel member 31 (FIG. 3). The flow channel member 31 is mounted within an assembly cartridge (not shown) under compression against the base 12 to effect a fluid seal along reference and form sample flow channels 34R and 34M for reference and sample liquids that flow over the ISE sensors 10 where 10R indicates a reference ISE sensor and 10M indicates a measuring ISE sensor.

Figure 2:
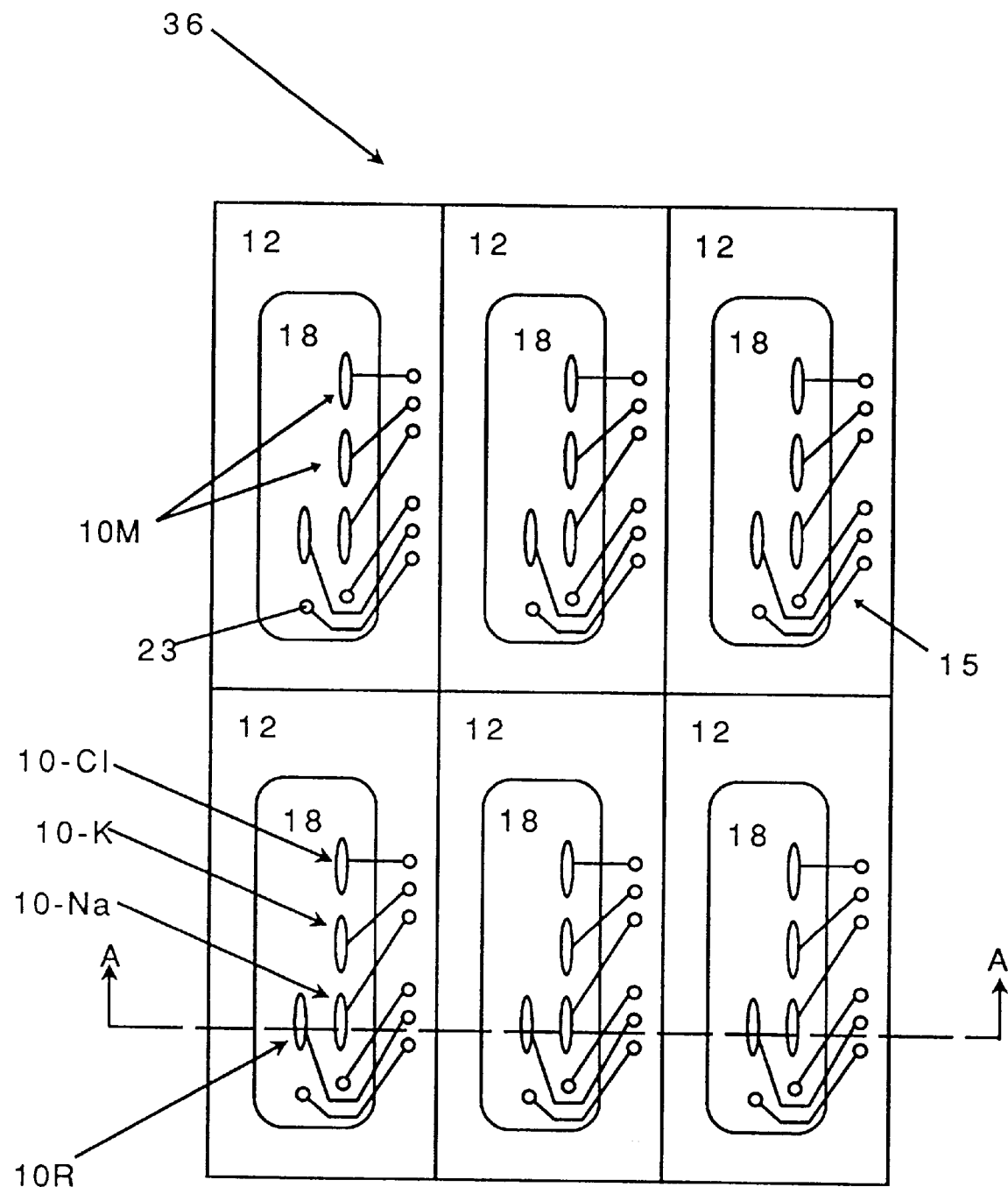
FIG. 2 is a plan view of a single sensor base supporting multiple ISE sensors; and, FIG. 3 is a partial cross sectional view of a sensor taken along the line A—A of FIG. 2

FIG. 2 shows a substrate 36 comprising a number of individual sensor bases 12 arrayed in a regular pattern, the bases 12 being defined by scribing a regular pattern onto a contiguously formed single manufacturing piece suitable for handling by automated production equipment. After manufacturing processes are completed, the sensor bases 12 may be separated into a number of individual sensors 10. Each of the sensor bases 12 has integrated thereon in planar arrangement an array of ISE sensors 10 comprising a plurality of conductive paths 15 deposited in patterns terminating in electrical contacting pads 23, sensors 10 also being comprised of individual layers 15, 16, and 17 (best seen in FIG. 1). FIG. 2 shows how the sensors 10 are designed to perform either reference or analyte measuring tasks and are preferably disposed in banks or rows with the sensors 10 being a reference function sensor 10-R being on one side or row and the sensor elements 10-Cl for measuring chloride, 10-Na for measuring sodium and 10-K for measuring potassium on the other side or row.

Each of the sensors 10 is individually connected by electrically conductive paths 15 which extend beyond the dielectric layer 14 to respective electrical contacts 23 which are formed on the top of the substrate 12. These contacts are located outside of the region that will be occupied by a flow channel member 31 which forms channels 34 over the respective sensor membranes 16 (FIG. 3). The contacts 23 are positioned so that they may be contacted by appropriate electrical connectors. The electrical connectors 15 are connected using contacts 23 to electronic circuitry within a chemical analyzer (not shown) which provides the as needed multiplexer and electrometer amplifiers to selectively connect the various pairs of sensors 10R and 10M so as to facilitate the various measurements necessary for the operation of the sensor.

FIG. 3 shows a pair of channels 32R and 32M that are separate from one another at a fluid inlet section but are joined together at a fluid egress end of each groove, thereby defining fluid flow channels 34R and 34M through which reference fluid used in a calibration procedure and sample fluid to be tested are able to flow through. The flow channel member 31 is formed of a material which is chosen to be chemically inert with respect to solutions likely to be used in the sensor cartridge. The upper surface of the sensor membrane layer 16 is thusly in fluid and electrolytic contact with reference fluids and sample fluids supplied through the fluid flow channels 34R and 34M, respectively. Elastomer materials such as butyl rubber, halobutyl rubber, bromobutyl rubber, silicone, polyurethane or polyvinyl chloride with room temperatures mechanical properties of hardness in the range of 40 Shore A (ASTM D-2140) to 60 Shore A and a segment modulus at 10% strain in the range 0.7 to 4.2 millipascals are preferred.

The amount of analyte in a sample liquid may be determined by using the sensor devices in pairs, with one sensor device being exposed to a reference or control fluid containing a known amount of analyte, and the other being exposed to a sample fluid containing an unknown amount of analyte. U.S. Pat. No. 5,184,568, assigned to the assignee of the present invention, is illustrative of such a device. Using well known calibration techniques, an assay may be performed in a comparative or differential method of measurement to determine the levels of an analyte in sample fluids.

Operation of the sensor 10 consists of a two point calibration procedure and then multiple test fluid analytical measurement steps. Both the two point calibration procedure and the sample measurements are comprised of two analytical determinations. The first calibration procedure step is typically accomplished by pumping a reference fluid, for example 1 molar KCl, into the reference flow channel 34R and then pumping a calibrator fluid into the measuring flow channel 34M. Calibrator fluids are solutions with known ionic concentrations within the range to be measured. A potential is then generated between the two sensors and measured by the electronics contained within the analyzer. The second calibration procedure step is accomplished by pumping a second calibrator fluid into the flow channel 34M. A potential is again generated and measured by the analyzer. The response or slope of the sensor is calculated from the measured potentials and the known ionic concentrations of the calibrator fluids.

The first sample fluid measurement step generally consists of pumping a sample fluid into the flow channel 34M and then drawing a reference fluid into the measuring flow channel 34R. A potentiometric signal is then measured. The second sample fluid measurement step consists of pumping the calibrator fluid into the flow channel 34M. A potentiometric signal is again measured. The concentration of the ion in the sample is calculated from the measured potentials and the known slope of the sensor and ionic concentration of the reference fluid.

As used in this specification, the term "fluid" includes liquids as well as gases, although at the present time liquids are primarily used. Also, although several reference sensor elements are shown, a single element can be used. The sensor elements may be along a curved path if desired.

The following examples are presented to illustrate sensor membranes exemplary of the practice of this invention.

EXAMPLES

Example 1

Quaternized Copolymer Synthesis from 15% Chloromethyl Styrene Copolymer

15% Chloromethyl Styrene Prepolymer Synthesis

A jacketed 250 mL four neck flask with circulating 80° water was equipped with a mechanical stirrer, water condenser, thermometer, nitrogen inlet/outlet and addition funnel. 80 mL of water was added, and the reaction vessel was flushed with nitrogen and stirred for 15 minutes. A mixture of 22.7 g of methyl methacrylate (85 mole-%), 6.1 g of chloromethyl styrene (15 mole %) and 95 $\mu$L of t-dodecanethiol was prepared.

Seventy two (72) mg of potassium persulfate and 77 mg of sodium dodecyl sulfate were added to the 80° stirred water, followed by 1.3 mL of the monomer mixture above. The reaction mixture was maintained at a temperature of 80° C., with stirring for 20 min. to allow nucleation of the emulsion. The remainder of the monomer mixture was then added at the rate of 1 mL/min., with stirring, while controlling the reaction temperature at 80° C.

After completion of the addition of the monomer mixture, the reaction temperature was maintained at 80° C. for an additional 30 min. The emulsion was coagulated by addition of 40 mL of methanol with vigorous stirring and refluxing. After cooling, the coagulated polymer slurry was filtered, washed 3× with 150 mL of water, 3× with methanol, and then 3× with water again. The product was dried in vacuo overnight.

Quaternized Polymer

Preferred Reaction Conditions: Twenty grams of the prepolymer was dissolved in 80 mL methylene chloride and 19.75 mL of tributyl amine. This was incubated at 30° C. for variable amounts of time, indicated in Table 1 below, to provide a solution of polymer with up to 100% conversion of the chloromethyl functionality. The polymer product of the quaternization reaction was purified by slowly adding the resulting mixture to one liter of a stirred 1:1 mixture of ethyl acetate and hexane. After the precipitation was complete, the product was filtered and washed with 400 mL of a 1:1 mixture of ethyl acetate and hexane. The product was dried in vacuo. Tg was measured and found to be in the range 55–60° C.

Example 1A

Alternate Reaction Conditions

Dimethyl sulfoxide was substituted for the dichloromethane reaction solvent used above. The product was isolated by precipitation into 0.1M HCl, instead of the ethyl acetate/hexane mixture. A dry granular product was obtained after washing with water by filtration, and drying.

Example 2

10% Quaternized Copolymer from 10% Chloromethyl Styrene Prepolymer

The polymerization described above was duplicated using a 90:10 mole % mixture of methyl methacrylate:chloromethyl styrene. 23.95 g of methyl methacrylate and 4.1 g of chloromethylstyrene were used. This copolymer was substituted directly into the quaternization reaction using dichloromethane as the solvent.

The concentration of quaternary ammonium groups in the polymer was determined by measurement of the ionized chloride freed from the chloromethyl styrene groups during quaternization. The quaternary ammonium chloride can be extracted into aqueous buffer by washing the powdered quaternized polymer with acidified sodium nitrate in water, whereas the chloride that is covalently bound to unreacted chloromethyl groups remains bound to the polymer. The chloride concentration in the aqueous extract can be measured using an ion selective electrode. Concentrations of quarternarized groups in polymer products from examples 1&2 are shown in Table 1.

TABLE 1

| Sample Number | Reaction Time (hours) | Mol. % Quaternary groups |
| --- | --- | --- |
| E88009-116B | 96 | 7.3* |
| E88009-116D | 96 | 7.4* |
| 09-109A | 50 | 12.7 |
| 09-109B | 115 | 14.5 |
| 09-109C | 164 | ND** |
| 09-109D | 214 | ND |
| E89471-124 | 216 | 15.4 |
| E89471-133 | 216 | 14.7 |
| E89471-141 | 216 | 14.7 |
| 71-55 | 216 | ND |
| 09-109E | 308 | ND |
| 10% Polymer (example 2)*** | 196 | ND |

*prepared in DMSO
**ND = not determined
***Prepared from copolymer made with 10 mole % chloromethylstyrene Unless otherwise indicated, the products listed above were prepared in the dichloromethane reaction solvent.

The concentration of quaternary ammonium groups in the products in the table above is expressed in units of mole percent of quaternized monomer units, where 100% is taken as the sum of the methyl methacrylate and chloromethyl styrene units.

Solutions of the quaternized polymers were prepared by mixing 1.01 g samples of the polymer and 1.25 mg of coumarin 6 with 4.01 g of diethyleneglycolmonoethyl ether, except in the case of the 10% product of Example 2. For this example, the solvent was a mixture of 3.21 g of diethyleneglycolmonoethyl ether and 0.81 g of isophorone. These solutions was used to prepare sensor membranes 16 for further testing. Coumarin 6 may be added to facilitate the optical alignment and inspection of the layers 16 and 17.

Sensor Test Results

The chloride sensors 10-Cl were one of four sensors 10 in an integrated array consisting of a sodium 10-Na, potassium 10-K, reference 10-R and chloride sensor 10-Cl illustrated in FIG. 3.

A quaternized layer 17 consisting of about 0.1 mg of quaternized polymer prepared as described hereinbefore was applied to the surface of the conventional chloride sensor 10-Cl membrane layer 16 of this array. As shown in FIG. 1, quaternized layer 17 substantially covered the sensor conventional membrane layer 16 without contacting the dielectric layer 18 to which the sensor membrane layer 16 is attached. Alternately, as shown in FIG. 1A, quaternized layer 17 incorporating quaternary ammonium groups as described hereinbefore is applied within the cavity 20 in contact with the conductive path 15. In both instances, solvent was removed by evaporation in a convection oven for one hour at 80° C.

The performance of sensors incorporating conventional chloride sensor 10-Cl membrane 16, membrane quaternized layer 17 (FIG. 1A) and conventional chloride sensor 10-Cl membrane 16 over coated with membrane quaternized layer 17 (FIG. 1) was determined by installing the integrated sensor arrays in cartridges on a Dimension® clinical chemistry analyzer sold by Dade International Inc., Newark, Del.

Two different instrument systems were used. In one, identified here as a "direct" measurement system, the sample was exposed to the sensors without prior dilution. In the second, identified here as an "indirect" measurement system, the sample measurement is done in exactly the same way as with the direct system, except that the instrument pre-dilutes every sample ten fold before applying it to the sensor.

The assembled cartridges were calibrated with two levels of each electrolyte, and then samples having two known levels of aqueous buffered electrolytes (verifiers) were analyzed to determine the selectivity and sensitivity characteristics of the chloride sensor 10-Cl having the quaternized layer 17 interposed between the conventional sensor membrane 16 and the sample fluid (FIG. 1) and to determine the sensitivity characteristics of the chloride sensor 10-Cl having only the quaternized layer 17 used in measuring ionic content of sample fluids (FIG. 1A).

Significant differences in sensor 10-Cl selectivity were observed with different levels of quaternary ammonium substitution within quaternized layer 17, when tested in the direct system. Hydrophobic anions are class of interfering substances that are found especially in urine samples, and that can lead to erroneous results with many chloride sensors designs. Sodium salicylate has been found to be a useful representative hydrophobic anion for challenging the performance of different chloride membrane compositions.

Sensors 10 having different levels of quaternary ammonium substitution within quaternized layer 17 were challenged first with salicylate free pooled human serum, and then with the same samples with 3 mM sodium salicylate added. In all cases, the salicylate caused some elevation of the measured chloride level. However, the errors due to salicylate were much larger for membranes 17 made with lower levels of quaternary ammonium substitution, even though the calibration slopes for all of the sensors were within 10% of each other, and all sensors gave the same response to the salicylate-free sample.

The different responses to the salicylate challenge are illustrated in Table 2.

TABLE 2

Sodium Salicylate Interference:

| Sample Number | Reaction Time (hours) | Mol. % Quaternary groups | Salicylate Interference (mM)* |
|---|---|---|---|
| E88009-116B | 96 | 7.3 | 8.9 |
| E88009-116D | 96 | 7.4 | 17.4 |
| 09-109A | 50 | 12.7 | 9.8 |
| 09-109B | 115 | 14.5 | 2.2 |
| 09-109C | 164 | ND** | 2.0 |
| 09-109D | 214 | ND | 2.0 |
| E89471-124 | 216 | 15.4 | 2.0 |
| E89471-133 | 216 | 14.7 | 1.9 |
| E89471-141 | 216 | 14.7 | 1.6 |
| 71-55 | 216 | ND | 2.2 |
| 09-109E | 308 | ND | 2.1 |
| 7FD872 (nominal 10%) | 216 | ND | 1.9*** |
| 6KD828 (nominal 15%) | 216 | ND | 2.5*** |

*Difference in CL result between pooled human serum containing ≈ 108 mM chloride, and the same pool spiked with 3 mM Sodium Salicylate, measured in the direct system unless otherwise indicated.
** = not determined
***Measured in the indirect system Surprisingly, it was found that the specificity relationship between salicylate interference and the concentration of quaternary ammonium groups in the polymer is not the same for the direct and indirect measurement systems. Polymer made with 10% loading gave better performance in indirect measurements than would be predicted from the response seen in the direct measurement system. More significantly, the accuracy of sensors made with the 10% loading was superior with clinical urine samples when the testing was done in the indirect system. This surprising result is illustrated in Table 3, with results from "problem" urine samples, comparing the accuracy of the direct measurement to those obtained with the two different copolymers as membranes in the indirect application:

TABLE 3

| Urine Sample ID # | Direct Measurement | Indirect Measurement (Using 13–15% Quat.) | Indirect Measurement (Using 8–10% Quat.) |
|---|---|---|---|
| U1 | 151.2 | 170.33 | 156.52 |
| U8 | 43.3 | 64.06 | 47.93 |
| U11 | 82 | 102.48 | 84.37 |
| U12 | 82.4 | 110.59 | 88.08 |
| U13 | 47.1 | 92.03 | 58.49 |
| U18 | 23.6 | 54.62 | 31.37 |
| U31 | 121.4 | 148.2 | 127.4 |
| U33 | 104.3 | 133.12 | 105.26 |
| U38 | 80.1 | 122.08 | 88.47 |
| U39 | 101.7 | 129.8i | 105.55 |
| U43 | 116 | 137.57 | 116.54 |
| u45 | 110.4 | 138.02 | 112.65 |
| u49 | 83.3 | 123.23 | 88.13 |

Stability testing:

Two types of stability testing were done to compare the performance of the polymer of this invention to the conventional TDMAC based sensor of the type described previously (U.S. Pat. No. 5,522,978 assigned to the assignee of the present invention). The first type of stability testing illustrates the effect on the sensor calibration slope of repeated exposure of the sensor to human plasma that contains heparin. The second type of stability testing illustrates the effect of prolonged exposure of the sensor to buffered saline on the accuracy of measurement of chloride in commercial control products.

Heparinized Plasma Exposure:

The stability of the sensor membranes when exposed to heparinized human plasma was determined for sensors having conventional TDMAC based membranes, and for sensors having the same design with an additional quaternized layer of quaternized polymer between the TDMAC containing layer and the sample. Integrated sensor arrays in cartridges were installed on a Dimension® clinical chemistry analyzer. The assembled cartridges were calibrated with two levels of each electrolyte, and then the cartridges were used 200 times with a sample of heparinized human plasma over a period of 10 about four hours. After completion of the 200 tests, the calibration was repeated. The slope of the calibration, in mV/decade of concentration of chloride, is a good indicator of the functionality of the sensor. If the slope changes by more than about 10% during use, the sensor performance becomes erratic, and may give inaccurate results with many samples.

Table 4 below illustrates the effect on the calibration slope of the chloride sensor of exposure to heparinized plasma using al three of the aforementioned TDMAC-based sensor designs.

TABLE 4

| Membrane Type | Initial Chloride Calibration Slope | Final Calibration Slope |
|---|---|---|
| TDMAC conventional design | −49.1 | −35.1 |
| Overcoat layer design without underlying TDMAC conventional design (FIG. 1A) | −47.0 | −47.4 |
| TDMAC conventional plus single quaternized layer design (FIG. 1) | −47.8 | −46.5 |

The conventional membrane based upon a single polymeric layer having TDMAC as the ion exchange material is clearly unstable in the presence of heparinized plasma; the calibration slope decreased by more than 15% during use with heparinized plasma samples. The single and bilayer designs, both having a polymeric layer with covalently bound quaternary ammonium groups retained the same calibration slope within experimental error after exposure to 200 samples of heparinized plasma.

Buffered Saline Exposure:

The stability to buffered saline exposure of chloride sensors with (FIG. 1) and without (FIG. 1A) the layer of polymer with covalently bound quaternary ammonium groups was compared. Cartridges were installed on a Dimension analyzer, calibrated, and tested with control products. After 96 hours of operation in standby, in which the sensors are exposed mainly to the buffered saline standards, the cartridges were recalibrated, and the testing with control products was repeated. The test results are shown for one control product, Monitrol® level 2, in Table 5 below:

TABLE 5

| Membrane Type | Initial Chloride found (0 hours) | Final Chloride found (96 hours) |
| --- | --- | --- |
| TDMAC conventional design | 94.8 mM | 101.3 mM |
| Bilayer design | 93.2 mM | 92.7 mM |

It is clear from the data above that, while the two designs agreed well initially, the conventional design drifted in response to the control product by about 6 mM, whereas the sensor with a membrane of the quaternary polymer of this invention did not drift significantly.

The stability to buffered saline exposure of chloride sensors having only membrane layer 17 comprising polymer with covalently bound quaternary ammonium groups was similarly measured by installing cartridges on a Dimension® clinical chemistry systems analyzer incorporating a sensor 10 with membrane design as shown in FIG. 1A. After 7 days of operation in standby, in which the sensor membrane layer 17 was exposed to only buffered saline solutions (MultiQual® Level 2), the cartridges were recalibrated, and the testing with control products was repeated. The test results are shown in Table 6.

TABLE 6

| TEST | Chloride Calibration Slope | After MultiQual ® Level 2 Exposure |
| --- | --- | --- |
| Day 1 | −47.8 | 103.9 mM |
| Day 2 | −46.6 | 102.9 mM |
| Day 3 | −46.1 | 103.3 mM |

Since the assigned value for the Monitrol® Level 2 is 102 mM, it is clear from the data above that the sensor membrane having a single layer 17 functioned as an acceptable chloride sensor without significant deterioration. In use, however, a sensor made using only the single layer 17 may be affected by interfacial interactions between the polymer and the electrode 15. For this reason, the sensor membrane structure having a conventional chloride membrane layer 116 interposed between the electrode 15 and the quaternized layer 17 is preferred.

It is to be understood that the embodiments of the invention disclosed herein are illustrative of the principles of the invention and that other modifications may be employed which are still within the scope of the invention. Accordingly, the present invention is not limited to the embodiments described in the specification but only by the following claims.

What is claimed is:

1. An ion-selective-electrode sensor membrane for determining the presence of chloride in fluids, the membrane comprising:

a first polymeric layer having a polymeric bonding material consisting of mixtures of methyl methacrylate and choloro-methyl styrene copolymer that have been reacted with tertiary amines and at least 8 mole-percent of quaternary ammonium groups covalently bound to said polymeric bonding material; and, a second polymeric layer comprising a chloride ionophore, wherein the first polymeric layer is positioned between the second polymeric layer and the fluids, thereby increasing the uselife of the selectivity and sensitivity of the membrane in the presence of interfering anions within the fluids.

2. The membrane according to claim 1 wherein the polymeric bonding material is quarternized with tertiary amines.

3. The membrane according to claim 1 wherein the polymeric bonding material is quarternized with tertiary amines to a degree of substitution at least as great as 14 mole-percent.

4. The membrane according to claim 1 wherein the polymeric layer comprises a polymeric bonding material selected from the group consisting of poly(vinyl chloride), carboxylated poly(vinyl chloride), poly(styrene-co-styrene sulfonic acid), poly(vinyl chloride-co-styrene sulfonic acid), poly(vinyl chloride-co-styrene carboxylic acid), and mixtures thereof.

5. The membrane according to claim 1 wherein the polymeric bonding material is prepared from a prepolymer reacted with tributylamine to provide the quaternary ammonium groups.

6. The membrane according to claim 5 wherein the prepolymer comprises methyl methacrylate, chloromethyl styrene, and t-dodecanethiol prepared by semicontinuous or continuous emulsion polymerization.

7. The membrane according to claim 1 wherein the polymeric bonding material is prepared from a prepolymer reacted with tributylamine to provide the quaternary ammonium groups.

* * * * *